United States Patent [19]
Ream

[11] Patent Number: 4,952,542
[45] Date of Patent: Aug. 28, 1990

[54] PROCESS FOR THE PRODUCTION OF ALKYLENE CARBONATE AND RECOVERY OF CATALYST

[75] Inventor: Bernard C. Ream, Charleston, W. Va.

[73] Assignee: Union Carbide Chemicals and Plastics Company Inc., Danbury, Conn.

[21] Appl. No.: 389,515

[22] Filed: Aug. 4, 1989

Related U.S. Application Data

[62] Division of Ser. No. 63,977, Jun. 19, 1987, Pat. No. 4,877,886.

[51] Int. Cl.⁵ .......................... B01J 38/60; B01J 38/62
[52] U.S. Cl. .......................................... 502/27; 502/28
[58] Field of Search ..................... 502/22, 24, 25, 26, 502/28

[56] References Cited

U.S. PATENT DOCUMENTS

| | | | |
|---|---|---|---|
| 4,219,338 | 8/1980 | Wolfs et al. | 502/24 |
| 4,391,735 | 7/1983 | Busse | 502/28 |
| 4,488,999 | 12/1984 | Feld | 502/24 |
| 4,598,057 | 7/1986 | Issacs | 502/33 |
| 4,607,121 | 8/1986 | Faggian et al. | 502/24 |
| 4,661,463 | 4/1987 | Mocella | 502/33 |
| 4,746,640 | 5/1988 | Erpenbach | 260/546 |
| 4,786,752 | 11/1988 | Holzhauer | 562/414 |

Primary Examiner—Anthony McFarlane
Attorney, Agent, or Firm—Norman L. Balmer

[57] ABSTRACT

Cyclic alkylene carbonates are produced by the homogeneous catalytic reaction of alkylene oxides with carbon dioxide during which process, polyglycols are formed. The catalyst is separated by distillation from the alkylene carbonate and is recycled to the reaction while associated with polyglycols. A purge stream is removed from the recycle to prevent an undue concentration of polyglycols in the reaction and catalyst is separated from the purge stream by acylation of the polyglycols enabling precipitation of the catalyst.

6 Claims, 1 Drawing Sheet

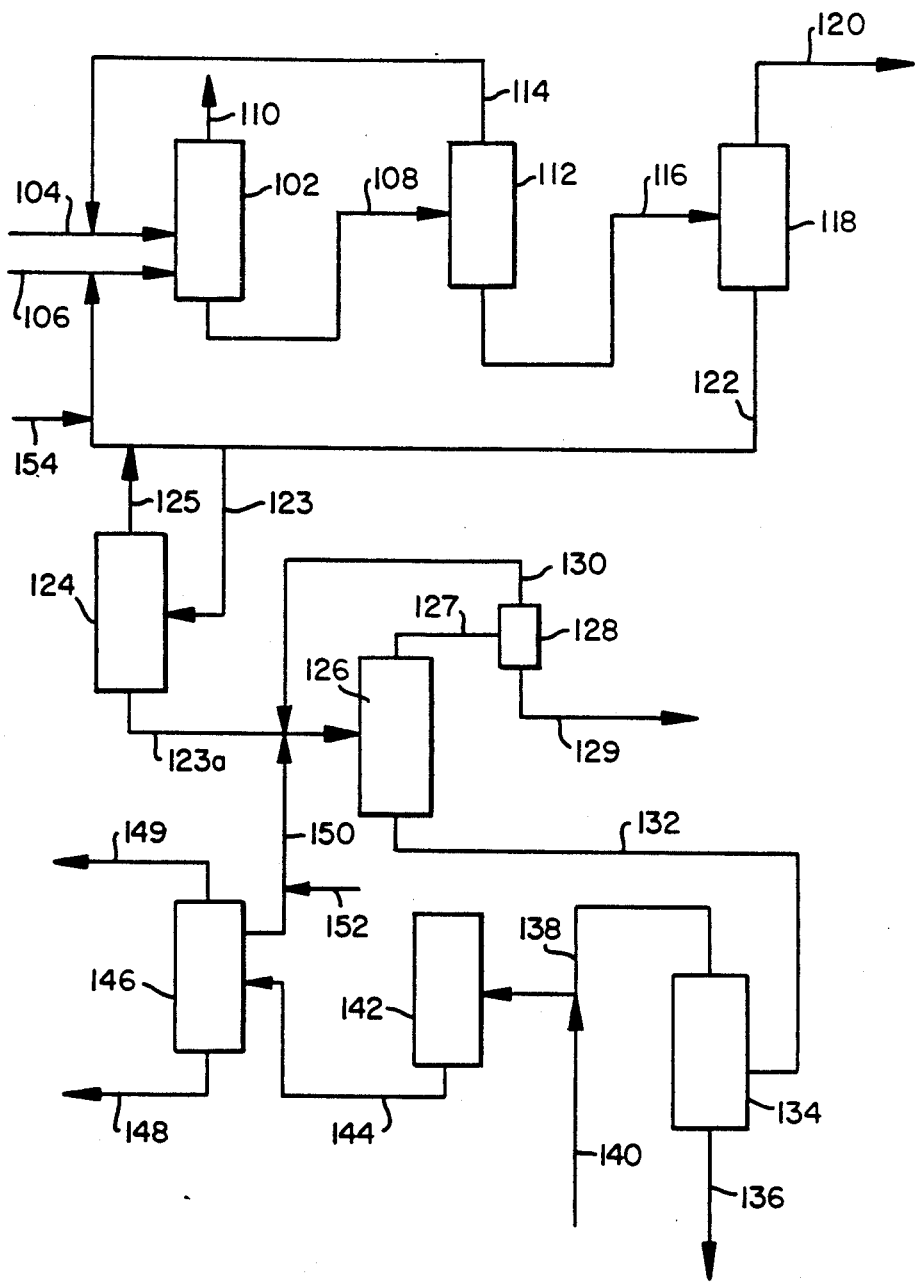

PROCESS FOR THE PRODUCTION OF ALKYLENE CARBONATE AND RECOVERY OF CATALYST

This application is a Division of prior U.S. application Ser. No. 063,977, filing date 6/19/87, now U.S. Pat. No. 4,877,886.

This invention relates to processes for the preparation of alkylene carbonates by the homogeneous catalytic reaction of alkylene oxide and carbon dioxide which processes exhibit reduced catalyst loss. In a broader aspect, the invention relates to processes for the recovery of inorganic cations from organohydroxide compounds.

BACKGROUND OF THE INVENTION

Alkylene carbonates can be prepared through the catalytic reaction of alkylene oxide and carbon dioxide. Alkylene carbonates are useful products and can be used as chemical intermediates or for shipment of alkylene oxide values wherein the alkylene carbonate is transported and subjected to thermal degradation to generate the alkylene oxide. Alkylene carbonates can also be hydrolyzed to form glycols in high selectivity and purity.

Alkylene oxides which have been proposed for the preparation of alkylene carbonates, e.g., see U.S. Pat. No. 2,773,070, issued Dec. 4, 1956, include those represented by the formula

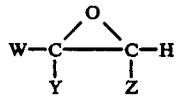

wherein W, Y and Z may be the same or different and may be hydrogen, alkyl of 1 to 20 carbon atoms, aryl of 6 to 12 carbon atoms, cycloalkyl containing 5 to 20 carbon atoms, alkenyl of 2 to 20 carbon atoms, and haloalkyl of 2 to 20 carbon atoms, and any of two of W, Y and Z may be interconnected to form with the two carbon atoms shown in the formula, a carbocyclic ring.

The formation of the cyclic carbonate has been by the catalytic reaction of carbon dioxide with alkylene oxide under elevated temperature and pressure in the presence of a catalyst. Numerous homogeneous catalysts have been proposed including ammonium halides (U.S. Pat. No. 2,773,070) and alkali and alkaline earth halides (U.S. Pat. Nos. 2,667,497 and 2,924,608, Japanese Patent Application No. Kokai 23175/63, published Oct. 31, 1963, and U.S.S.R. Author's Certificate No. 170,529, published Apr. 23, 1965 by S. Z. Levin and A. L. Shapiro).

In order to provide an attractive process for the preparation of alkylene carbonates, the process should be capable of achieving high selectivity to alkylene carbonate and should be economically sound. For example, when ethylene oxide is used to form ethylene carbonate which is then hydrolyzed to form ethylene glycol or decomposed to form ethylene oxide, a viable commercial process will be characterized as one which does not incur undue additional costs over the production of ethylene oxide or ethylene glycol directly from the hydrolysis of ethylene oxide. Many factors affect the economics of alkylene oxide manufacture, and one of these factors is the ability to recover and reuse catalyst for the formation of alkylene carbonate.

For purposes of illustration, reference shall be made to continuous processes for the preparation of ethylene carbonate from ethylene oxide using a potassium iodide catalyst. See U.S. Pat. No. 4,314,945, issued Feb. 9, 1982, herein incorporated by reference, for further background information. In these types of processes, ethylene oxide is reacted with carbon dioxide at a temperature of up to about 200° C. under carbon dioxide pressure in the presence of about 0.1 to 3 weight percent potassium iodide. Selectivities of greater than 99 percent with 99.5 percent conversion can be obtained. The catalyst may then be removed from the reaction product by distillation and returned to the carbonate-forming reaction zone. During the reaction, other products are formed, albeit in small amounts, and, because of their high boiling temperatures, may be recycled with the catalyst. These other products frequently include polyglycols. Polyglycols that are recycled with the catalyst can lead to an undesirable build-up of polyglycols within the reaction zone. Polyglycols are believed to enter into undesirable reactions in the carbonate-forming reaction zone that not only affect the efficiency of the process but also can deleteriously affect the quality of the alkylene carbonate. To prevent a build-up of other products recycling with the catalyst, a purge stream may be taken. This, however, can result in the loss of catalyst unless catalyst is recovered from the purge stream. For instance, for the sake of a perspective to the significance of loss of catalyst, in a plant producing 140,000 metric tons of ethylene carbonate per year, a purge stream can result in a removal of about 35 pounds of potassium iodide per hour. At a price of potassium iodide of $10 per pound the value of catalyst lost could be about $2,000,000 per year.

Unfortunately, catalysts such as potassium iodide are not readily recovered from polyglycols contained in the purge since potassium iodide is highly soluble in polyglycols. For example, the solubility of potassium iodide in a synthesized glycol mixture (25.10 weight percent monoethylene glycol, 12.95 weight percent diethylene glycol, 7.16 weight percent triethylene glycol, 9.69 weight percent tetraethylene glycol, 38.72 weight percent ethylene glycol, and 5.06 weight percent hexaethylene glycol) is about 27 weight percent at 25°, 130° and 160° C. Indeed, no precipitation of potassium iodide was observed at dry ice-acetone temperature (−78° C.) or at 190° C. This solubility is believed to be due to the chelating effect of the glycols on potassium iodide. Accordingly, an effective system is sought to recover catalyst from such purge streams.

SUMMARY OF THE INVENTION

By this invention processes are provided for the catalytic conversion of alkylene oxides to alkylene carbonates in which polyglycols are formed. In the processes, catalyst is recovered from the alkylene carbonate product and recycled for use in the catalytic conversion and polyglycols are carried with the catalyst being recycled, a purge stream is taken to prevent untoward amounts of polyglycol in the catalytic conversion and catalyst is recovered from the purge stream. In the processes, the polyglycol-containing purge stream is subjected to acylating conditions sufficient to reduce the solubility of the catalyst in the purge stream and at least a portion of the catalyst is separated as a solid therefrom.

In preferred aspects of the invention, the acylation is conducted while removing water from the menstruum to assist in driving the acylation reaction toward completion. In many instances, it is desired to provide the acylated purge at an elevated temperature sufficient to enhance the precipitation of catalyst from the purge.

While the invention has been described with reference to the production of alkylene carbonates from alkylene oxides, the processes of the invention have applicability to other processes for the recovery of soluble salts of inorganic cations from liquid media containing organohydroxide compounds. In its broadest aspects, the invention provides for the separation of a salt of an inorganic cation, e.g., ammonium, alkali or alkaline earth metal, from organohydroxide compound-containing liquid medium by the steps comprising contacting the organohydroxide compound-containing medium with sufficient amount of an acylating agent comprising at least one lower organic acid and organic acid anhydride under acylating conditions to acylate the organohydroxide compound and reduce the solubility of the salt in the organohydroxide compound-containing liquid medium and thereby precipitate the salt and separating the precipitated salt from the organohydroxide compound-containing medium.

DETAILED DISCUSSION

The salts that may be present in the organohydroxide compound-containing medium can vary widely. Often, the salts are highly soluble in the medium, e.g., in amounts of at least about 10, say, at least about 20, and sometimes at least about 50, grams per liter at 25° C. With respect to some of the salts and some of the organohydroxide compounds, this high solubility exists over a broad temperature range. This is believed to be caused by a chelating effect between the organohydroxide compounds and the salts.

Typical cations of the salts include ammonium, alkali metal such as lithium, sodium, potassium, rubidium and cesium, and alkaline earth metal such as magnesium, calcium and barium. Other cations such as aluminum and copper may find applicability as well. Included within the ammonium cations are the quaternary ammonium cations, for instance, lower tetraalkylammonium cations wherein each alkyl has 1 to about 6 carbons. The preferred cations are the alkali metal ions, e.g., sodium, potassium, rubidium and/or cesium. The anions may be halide; oxyanion such as sulfate, phosphate, carbonate, bisulfate, molybdate, vanadate, tungstate, and the like; sulfide; or mercaptide wherein the organo group has from one to six carbons. Exemplary of the salts that have found particular utility in the conversion of alkylene oxides to alkylene carbonates are the ammonium, tetraalkylammonium and alkali metal salts of anions more nucleophilic than chloride, e.g., bromide and iodide with iodide being preferred. Representative of these salts are potassium bromide, potassium iodide, tetraethylammonium bromide, tetraethylammonium iodide, and the like.

The concentration of the salts in the organohydroxide compound-containing medium can vary widely, and the salts are often present in amounts of about 0.0001 to 50 weight percent, e.g., about 0.001 to 30 weight percent.

The organohydroxide compounds involved in the processes of this invention are characterized as having at least one hydroxy group and include alcohols, diols and polyols. The organohydroxide compounds frequently contain at least one other hetero atom such as oxygen or nitrogen as in ethers or amines. The organohydroxide compounds often contain one to about 30 carbon atoms. Representative organohydroxide compounds include alcohols such as methanol, ethanol, n-propanol, i-propanol, n-butanol, i-butanol, t-butanol, etc.; glycols such as ethylene glycol, 1,2-propylene glycol, 1,3-propylene glycol, 1,2-butanediol, 1,4-butanediol, diethylene glycol, triethylene glycol, tetraethylene glycol, pentaethylene glycol, dipropylene glycol, etc.; alkanolamines such as monoethanolamine, diethanolamine, triethanolamine, etc.; and the like.

The organohydroxide compound frequently comprises at least about 20 volume percent of the liquid medium, and more frequently, about 50 to 95 or more volume percent. Other compounds may be present in the medium depending upon the origin of the organohydroxide compound.

The acylating agents are preferably organoacids and anhydrides. The preferred acylating agents have from 1 to about 16, preferably 2 to about 10 carbon atoms and one or two acid moieties. Preferably the acylating agent is soluble in the organohydroxide compound-containing medium. Often the acylating agent and the organohydroxide compound are completely miscible at all proportions. Representative acylating agents are formic acid, acetic acid, acetic acid anhydride, propionic acid, propionic acid anhydride, butyric acid, maleic acid, maleic acid anhydride, phthalic acid, phthalic acid anhydride, succinic acid, succinic acid anhydride, etc. Acid acylating agents are preferred over anhydrides. The acylating agent should be selected such that the acylated, organohydroxide compound is in the liquid phase, and preferably is dissolved in the medium, during the precipitation of the salt. Advantageously, the acylating agent is soluble in the acylated, organohydroxide compound.

The acylating agent is provided in amounts sufficient that the solubility of the salt in the organohydroxide compound-containing medium is reduced and enable salt to precipitate. Advantageously, the acylating agent is provided in an amount substantially in excess of that required for reaction on a stoichiometric basis with the reactable moieties in the organohydroxide compound containing medium. (The reactable moieties may include other than the hydroxide groups of the organohydroxide compound, e.g., acids may also be present.) Sometimes the mole ratio of hydroxy groups on the organohydroxide compound to acylating agent moieties is from about 0.25 to 50, more frequently, about 0.75 to 10.

The acylation is generally conducted at elevated temperature, e.g., about 50° to 250° C., preferably about 70° to 150° C. When the organohydroxide compound is believed to chelate with the salt, the temperature during acylation should not only be sufficient to effect the acylating reaction at a desirable rate but also to sufficiently weaken or break the chelating bond to permit the acylation to occur. The acylation can be conducted at subatmospheric, atmospheric or superatmospheric pressure, e.g., from about 0.01 to 20 bar absolute. The acylation, if desired, may be conducted under agitation.

The acylation is, as a general rule, an equilibrium reaction. Accordingly, the presence of components that adversely affect the reaction toward the acylated product should be minimized. Thus, for instance, water is generally present in the organohydroxide compound-containing medium in relatively small amounts. Especially when employing acids as the acylating agent, water is removed during the acylation to drive the reaction toward the acylated product. The drying may be effected by distillation or drying agents such as molecular sieves and may be conducted within the acylating reaction vessel or a slip stream may be treated to remove the water and recycled to the reaction vessel. Frequently, the organohydroxide compound-containing medium contains less than about 5, preferably less than about 2, say, less than about 0.5, volume percent water. In some instances it may be desired to effect the water removal by azeotropic distillation and azeotroping agents such as benzene, toluene and xylene may be used.

The extent of the acylation will be determined by the economics and processing considerations. The processes of this invention provide the use with wide latitude of operation, with the more complete the acylation, the greater the amount of recovery of the salt. In most instances it is desired to recover at least about 40 percent of the salt, preferably about 50 to 99 percent of the salt. The acylation may be conducted over a relatively short period of time thus making it attractive for continuous processes. For instance, the residence time of the organohydroxide compound-containing medium in the acylation zone may be less than about 1 hour, e.g., between about 30 seconds and 0.5 hour.

As the acylation proceeds, particularly in processes in which water is removed or otherwise maintained at relatively low concentrations during the acylation, salt usually precipitates. In some instances it may be desirable to form the precipitate or form additional precipitate by changing the temperature of the medium or by removing additional components from the medium. For example, since the salt is usually soluble in water, any water remaining in the medium after acylation may be removed to achieve additional precipitation. It has been found that in some instances, especially those in which the organohydroxide compound is believed to chelate the salt, the salt is less soluble in the acylated medium at elevated temperatures than at ambient temperatures. In these instances, elevated temperatures, e.g., about 125° to 300° C. may be desirable to enhance the formation of precipitate. In other instances, lower temperatures favor the formation of precipitate.

The precipitate may be recovered from the medium by any convenient means. Separation mechanisms include settling and filtration. The filtrate can be hydrolyzed to generate acid which can be recovered from the organohydroxide and used as an acylating agent.

BRIEF DESCRIPTION OF THE DRAWING

The disclosed FIGURE is a preferred embodiment of the invention.

PRODUCTION OF ALKYLENE CARBONATE

The invention will be further described with reference to a process for the production of alkylene carbonate from alkylene oxide. In this description reference will be made to the FIGURE which is a schematic representation of a process operating in accordance with this invention. In the FIGURE, equipment not essential to the understanding of the invention such as heat exchangers, pumps, and the like have been deleted.

With reference to the FIGURE, reactor 102 is a back mix reactor although a plug flow reactor may also be used, in which the alkylene oxide is reacted with carbon dioxide to form alkylene carbonate. Preferably the reactor is stirred to enhance contact of the components and provide more uniform temperature control. Reactor 102 is charged with carbon dioxide via line 104 and alkylene oxide and catalyst via line 106. The alkylene oxide may be an alkylene oxide of the type disclosed in U.S. Pat. No. 2,773,070 described above.

The preferred alkylene carbonates can be represented by the formula:

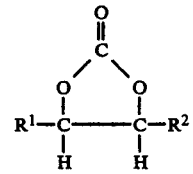

wherein $R_1$ and $R_2$ may be the same or different and are selected from the group consisting of hydrogen and alkyl of 1 to 6 carbons and $R_1$ and $R_2$ may form a cyclic structure. These alkylene oxides can be represented by the formula:

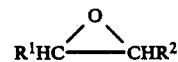

wherein $R^1$ and $R_2$ are as defined above. For purposes of discussion, ethylene oxide will be the alkylene oxide and ethylene carbonate, the product.

The catalyst will be potassium iodide; however, it is recognized that other salts such as potassium bromide, ammonium iodide, ammonium bromide, tetraethylammonium bromide, tetraethylammonium iodide, cesium iodide and cesium bromide could also be used. The catalyst is homogeneous, i.e., it is dissolved in the liquid medium.

The carbon dioxide is usually provided to a pressure of about 10 bar absolute to 80 bar absolute. The amount of carbon dioxide dissolved in the liquid is often about 0.1 to 6 weight percent based on the total weight of the liquid phase. The catalyst is typically provided in an amount of about 0.1 to 10 weight percent, based on the total weight or reactants and product in the reactor. Generally, the catalyst is present in amounts of about 0.2 to 3 weight percent, based on total reactants and products in the reactor. Preferably, the amount of carbon dioxide dissolved in the liquid in the reactor exceeds, on a molar basis, the amount of catalyst present.

The carbonate reaction is most often conducted using the product, the ethylene carbonate, as the solvent. Ethylene carbonate is a good solvent for the reaction and does not have to be separated from the reaction product, thereby simplifying the process. Typically, the ethylene carbonate comprises between about 85 to 99.6 weight percent of the total weight within the reaction zone.

The reaction of ethylene oxide and carbon dioxide is exothermic and the temperature of the reaction zone is usually maintained below about 200° C. to enhance product quality. Generally, the reaction temperature is between about 100° C. and 200° C.

The ethylene carbonate product is withdrawn from reactor 102 via line 108. Also provided on reactor 102 is vent line 110 which can be operated continuously or intermittently to purge the reactor of volatile impurities which could be deleterious to the product quality. For example, in the case of ethylene carbonate manufactured from ethylene oxide, acetaldehyde is formed and can be removed via a reactor vent. Acetaldehyde, if it remained in the reaction zone, could undergo further reactions to form polymeric materials and/or ultraviolet absorbers which detract from product quality. The reaction also produces alkylene glycols which may be represented by the formula

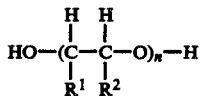

wherein $R_1$ and $R_2$ are as defined above and n is 1 to about 8, viz., ethylene glycol, diethylene glycol and polyglycols.

The ethylene carbonate-containing product is fed from line 108 into separator 112 from which volatile carbon dioxide is separated and returned to reactor 102 via lines 114 and 104. The separator is typically at a pressure of between about 10 and 80 bar absolute and a temperature of between about 50° or 75° and 200° C.

The liquid from separator 112 is passed via line 116 to distillation column 118 from which ethylene carbonate is recovered as the vaporous effluent which exits via line 120 and the bottoms contain the catalyst. The distillation column is usually operated at a pressure of between about 0.04 and 0.08 bar absolute such that the bottoms temperature can be maintained below about 130° C. and thereby mitigate undue degradation of the ethylene carbonate product or the other components in the distillation column. Impurities such as ethylene glycol and diethylene glycol have sufficiently low vapor pressures that a significant portion are often removed with the ethylene carbonate product.

The bottoms often contain from about 0.1 to 20, more frequently, 1 to 10 weight percent catalyst with the remainder comprising about 0.5 to 50, say, about 5 to 40, weight percent polyglycol components formed as a result of the carbonate-forming reaction and subsequent processing. The bottoms will also contain ethylene carbonate, e.g., ethylene carbonate will usually comprise between about 40 and 90, say, 65 to 85, weight percent of the bottoms. Ethylene glycol and diethylene glycol are also usually present, e.g., in amounts of about 5 to 60 or more, weight percent of the bottoms.

The bottoms which contains catalyst is recycled to reactor 102 via line 122 and 106. A purge stream is removed from line 122 via line 123 in an amount sufficient to maintain a constant concentration of the polyglycol components in reactor 102. Generally, the concentration of polyglycol in the reactor is between about 0.1 and 10, usually, about 2.5 and 7.5, weight percent based on the total weight of liquid in the reactor. Frequently, the purge stream is about 5 to 50, say, about 15 to 30, weight percent of the bottom stream from distillation column 118.

The purge stream in line 123 is passed to thermal decomposer 124 in which the contained ethylene carbonate is thermally degraded to ethylene oxide and carbon dioxide. The thermal degradation is usually conducted at a temperature of about 170° to 220° C. and a pressure of between about 0.04 and 0.25 bar absolute. The thermal degradation conditions are usually at least sufficient to enable recovery of at least 70, preferably, about 75 to 99, mole percent of the ethylene oxide values from the ethylene carbonate in the purge. Frequently, the residence time of the purge stream in the thermal decomposer is from about 2 seconds to 30 minutes, say, about 10 seconds to 5 minutes.

The vaporous effluent from thermal decomposer 124 contains ethylene oxide and carbon dioxide and is depicted as being passed from thermal decomposer 124 via line 125 to line 122 for recycle to reactor 102. The liquid from thermal decomposer 124 is an organohydroxide compound-containing medium and is passed via line 123a to acylation reactor 126. The polyglycols from the thermal decomposer frequently comprise about 2 to 50 weight percent triethylene glycol, about 2 to 50 weight percent tetraethylene glycol, about 2 to 50 weight percent pentaethylene glycol and about 2 to 50 weight percent, cumulative, polyethylene glycol higher than pentaethylene glycol. While ethylene glycol and diethylene glycol, not conventionally considered to be polyglycols for the purposes herein since they do also solubilize potassium iodide and are present, are considered to comprise the polyglycol fractions.

In acylation reactor, acetic acid is reacted with the polyglycols to reduce the solubility of potassium iodide. As depicted, the acylation reactor is maintained under azeotropic distillation conditions to continuously remove water from the reaction zone. The azeotroping agent, for purposes of illustration, is toluene, and thus the acylating reactor is maintained at a temperature of about 85° to 150° C. and pressure of about 1 to 30 bar absolute. With other azeotroping agents, other temperatures and pressures may be used. However, to facilitate the acylation reaction, it is preferred that the reaction temperature be maintained above the boiling point of water at the pressure of the reactor, say, between about 100° and 125° C. The amount of azeotroping agent in the reactor may vary. However, generally about 30 to 70 weight percent of the contents of the reactor are azeotroping agent. The azeotrope is removed from acylating reactor 126 via line 127 and passed to separator 128 in which a water fraction and organic fraction forms. The water is removed via line 129 and organic layer is returned via line 130 to the acylation reactor. The organic layer will often contain acetic acid. Other azeotroping agents that can be used include benzene and xylene.

The acylated product from the acylation reactor exits via line 132 to filter 134 in order to remove precipitated potassium iodide. Preferably, the acylated product is kept warm, or heated (depending upon the acylating temperature) e.g., to provide a temperature of at least about 150° C., preferably 170° C. to 250° C. At these elevated temperatures, the solubility of potassium iodide is less than at lower temperatures. The filter medium often is capable of retaining particles having an average dimension of at least about 5 microns. The solids are removed from filter 134 as shown by line 136. The particles may be returned to reactor 102; however, to avoid the introduction of impurities into the reactor, it is desirable to wash the potassium iodide prior to returning it to the reactor.

The filtrate from filter 134 is passed via line 138 to hydrolysis reactor 142 in which water added via line 140 reacts with the acylated components to regenerate acetic acid. This hydrolysis reaction is often conducted at a temperature of from about 75° to 150° C. and a pressure from about 0.5 to 20 bar absolute. Frequently, the water is provided in excess of that required for stoichiometric reaction with the acyl groups. The mole ratio of water to acyl groups is usually between about 0.5:1 to 50:1.

The hydrolyzed product exits reactor 142 via line 144 and is passed to distillation system 146. In distillation system 146, water is removed from the acetic acid and polyglycols and the acid and polyglycols are separated with the polyglycol fraction being discharged via line 148 and the acetic acid being recycled to the acylation reactor via line 150. Make-up acetic acid or acetic acid anhydride is provided via line 152.

With reference to line 122, the catalyst-containing ethylene carbonate stream which is recycled to reactor 102 is depicted as having make-up catalyst fed via line 154 into it.

EXAMPLE

A simulated polyglycol residue is provided. Gas chromatography analysis of a silylated sample of the material showed that it had the following composition.

| Component | Weight Percent |
| --- | --- |
| Monoethylene glycol | 25.10 |
| Diethylene glycol | 12.95 |
| Triethylene glycol | 7.16 |
| Tetraethylene glycol | 9.69 |
| Pentaethylene glycol | 38.72 |
| Hexaethylene glycol | 5.06 |

Potassium iodide was added to a weighed amount of the polyglycol sample at the desired temperature until there was an insoluble excess. The solution was filtered at the temperature specified below; the amount of soluble KI was determined by subtracting the weight of the insoluble excess from the total amount of KI added. The results of the solubility experiments are tabulated below.

| T (°C.) | KI (Wt. %) |
| --- | --- |
| 25* | 26.67 |
| 130 | 27.48 |
| 160 | 26.97 |

*Dissolution was exothermic, causing the temperature to rise to 37° C.; this effect was not observed at the two higher temperatures.

A mixture of 20.0 g of KI/polyglycol sample (27.7% KI), 30.0 g of glacial acetic acid, and 45 ml of toluene was charged to a 125 ml Erlenmeyer flask, equipped with a magnetic stirrer, a Dean Stark azeotropic distillation head, a thermometer, and a condenser. The Dean-Stark trap was filled with toluene and the mixture was refluxed overnight (about 12 hours) at 102° C. During this time, the volume of the bottom layer of the azeotrope equilibrated at 12.0 ml. The composition of the bottom layer of the azeotrope was:
19.50% water
51.27% acetic acid
29.23% toluene Excess toluene and acetic acid were distilled overhead and the temperature of the homogeneous kettle residue was raised from 102° to 190° C., where KI precipitated from solution. The hot solution was filtered through a steam-jacketed Buchner funnel and the solid was washed with cold ethyl acetate. The washings were concentrated, the concentrate was reheated to 190° C., and a second batch of solid precipitated. The solids were combined and dried at 100° C. overnight in a vacuum oven, giving 5.17 g (95.7%) KI recovery.

X-ray diffraction patterns of the recovered KI and the starting KI reagent were identical.

A. Cycle #1

A mixture of 20.00 g of KI/polyglycol sample (27.7% KI) 28.32 g (0.472 mol) of glacial acetic acid, and 56.6 g of toluene was charged to a 125 ml Erlenmeyer flask, equipped with a magnetic stirrer, a Dean Stark azeotropic distillation head, a thermometer, and a condenser. The Dean Stark trap was filled with 80/20 (w/w) toluene/acetic acid and the mixture was refluxed overnight (about 12 hours) at 102° C. During this time, the volume of the bottom layer of the azeotrope equilibrated at 11.4 ml. The amounts and compositions of the layers were as follows:

| Layer | Vol(ml) | Wt(g) | Composition (wt. %) | | |
| --- | --- | --- | --- | --- | --- |
| | | | Toluene | Acetic Acid | Water |
| Top | 100 | 88.5 | 85.71 | 13.81 | 0.48 |
| Bottom | 11.4 | 12.0 | 40.80 | 40.08 | 19.12 |

Excess toluene and acetic acid were distilled overhead and the homogeneous kettle residue (at 102° C.) was heated to 190° C., at which temperature solid KI precipitated out of solution. The hot solution was filtered through a steam-jacketed Buchner funnel and the solid was washed with cold ethyl acetate. After drying in a vacuum oven at 100° C. overnight, 4.42 g (81.9%) of KI were recovered.

B. Cycle #2

The second cycle was run like the first cycle except that the starting solutions had the following compositions.

Reaction Flask 200.00 g of KI/polyglycol sample (27.7% KI)
66.1 g of the top layer of the azeotrope generated in cycle #1
19.2 g of glacial acetic acid Dean Stark Trap 21.6 g of 85/15 toluene/acetic acid The amounts and compositions of the two layers of the azeotrope generated in cycle #2 were as follows:

| Layer | Vol(ml) | Wt(g) | Composition (wt. %) | | |
| --- | --- | --- | --- | --- | --- |
| | | | Toluene | Acetic Acid | Water |
| Top | 96.0 | 83.6 | 84.92 | 14.80 | 0.28 |
| Bottom | 11.5 | 11.9 | 32.23 | 47.35 | 20.42 |

Recovered KI was 4.98 g (92.2%).

C. Cycle #3

The third cycle was run like the second cycle except for the following differences.

Reaction Flask 66.1 g of the top layer of the azeotrope generated in cycle #2
18.7 g of glacial acetic acid The amounts and compositions of the two layers of the azeotrope generated in cycle #3 were as follows:

| Layer | Vol(ml) | Wt(g) | Composition (wt. %) | | |
|---|---|---|---|---|---|
| | | | Toluene | Acetic Acid | Water |
| Top | 98.0 | 86.3 | 85.84 | 13.70 | 0.46 |
| Bottom | 11.4 | 11.7 | 24.60 | 51.50 | 23.60 |

Recovered KI was 5.12 g (94.8%).

TABLE I

**KI RECOVERY FROM POLYGLYCOL RESIDUES[a]
RECYCLE OF THE TOLUENE-RICH PHASE OF THE
TOLUENE-ACETIC ACID-WATER AZEOTROPE**

| Cycle No. | Reactor Charge (g) | | | Dean-Stark Trap Charge (g) | | Recovery (%) | Layer | Azetrope Compositions (Weight Percent) | | |
|---|---|---|---|---|---|---|---|---|---|---|
| | Toluene | HOAc | KI/Polyglycols[b] | Toluene | HOAc | | | Toluene | HOAc | $H_2O$ |
| 1 | 56.6 | 28.32 | 20.0 | 17.3 (80:20) | 4.3 | 81.9 | Top | 85.71 | 13.81 | 0.48 |
| | | | | | | | Bottom | 40.80 | 40.08 | 19.12 |
| 2 | 56.7 | 28.33 | 20.0 | 18.4 (85:15) | 3.2 | 92.2 | Top | 84.92 | 14.80 | 0.28 |
| | | | | | | | Bottom | 32.23 | 47.35 | 20.42 |
| 3 | 56.7 | 28.48 | 20.0 | 18.4 (85:15) | 3.2 | 94.8 | Top | 85.84 | 13.70 | 0.46 |
| | | | | | | | Bottom | 24.60 | 51.80 | 23.60 |

[a]Reaction Conditions: Reflux at 102° C. for about 12 hours.
[b]KI/Polyglycols sample contained 27.7% (by wt.) of KI.

It is claimed:

1. A process for the separation of a salt having an inorganic cation from a liquid medium in which said salt is soluble and which liquid medium contains organohydroxide compound comprising contacting the liquid medium with sufficient amount of acylation agent comprising at least one lower organic acid having from 1 to 16 carbon atoms or acid anhydride under acylating conditions to acylate at least a portion of the organohydroxide compound and to reduce the solubility of the salt in the liquid medium and form precipitate of the salt, and separating precipitated salt from the acylated liquid medium.

2. The process of claim 1 wherein the inorganic cation comprises alkali or alkaline earth ion.

3. The process of claim 1 wherein the organohydroxide compound is a glycol.

4. The process of claim 1 wherein the acylated liquid is provided at a temperature in the range of from about 50° to 250° C. while precipitating the salt.

5. The process of claim 1 wherein the acylating agent comprises a lower organic acid having from 1 to 16 carbon atoms.

6. The process of claim 5 wherein water is produced during the acylation and is removed from the liquid medium during the acylation.

* * * * *